(12) United States Patent
Massey et al.

(10) Patent No.: US 6,929,368 B2
(45) Date of Patent: Aug. 16, 2005

(54) METHOD FOR DETERMINING THE SUITABILITY OF A TRANSPARENT MOULDED POLYMER ARTICLE FOR COLORING WITHOUT DEFECTS AND RESULTING ARTICLE

(75) Inventors: Gilles Massey, Saint-Maur (FR); Jean-Claude Dauguet, Marolles en Brie (FR)

(73) Assignee: Essilor International Compagnie Generale d'Optique, Charenton cedex (FR)

( * ) Notice: Subject to any disclaimer, the term of this patent is extended or adjusted under 35 U.S.C. 154(b) by 486 days.

(21) Appl. No.: 09/972,396

(22) Filed: Oct. 5, 2001

(65) Prior Publication Data

US 2002/0081375 A1 Jun. 27, 2002

Related U.S. Application Data

(63) Continuation of application No. PCT/FR00/00842, filed on Apr. 5, 2000.

(30) Foreign Application Priority Data

Apr. 6, 1999 (FR) .......................................... 99 04268

(51) Int. Cl.$^7$ ................................................ G02C 7/10
(52) U.S. Cl. ........................................ 351/177; 8/506
(58) Field of Search ................................ 351/163, 177; 8/506, 507

(56) References Cited

U.S. PATENT DOCUMENTS

| | | | | |
|---|---|---|---|---|
| 4,241,102 A | | 12/1980 | McKinley et al. ............ 209/3.1 |
| 4,303,701 A | | 12/1981 | Torgersen et al. ........... 427/145 |
| 4,320,939 A | * | 3/1982 | Mueller ........................ 351/44 |
| 4,329,378 A | * | 5/1982 | Tarumi et al. ............... 427/157 |
| 4,632,773 A | * | 12/1986 | Neefe ..................... 252/301.35 |
| 4,695,399 A | | 9/1987 | Neefe ..................... 252/301.35 |
| 5,201,921 A | | 4/1993 | Luttermann et al. ............ 8/506 |

FOREIGN PATENT DOCUMENTS

| | | |
|---|---|---|
| EP | 0838850 | 4/1998 |
| WO | WO 00/60395 | 10/2000 |

* cited by examiner

Primary Examiner—Scott J. Sugarman
(74) Attorney, Agent, or Firm—Fulbright & Jaworski L.L.P.

(57) ABSTRACT

The method comprises:

a) placing in contact at least one principal surface of the colourless articles of the set with a solution of a fluorescent material for a sufficient time to allow penetration of the fluorescent material under the principal surface of the article;

b) irradiation of the impregnated articles by means of radiation which activates the fluorescence of the fluorescent material; and c) selection of the articles in the set into two sub-sets of which the first is composed of those articles of the set which show a homogeneous fluorescence of their principal surfaces under irradiation and the second is composed of those articles of the set which show a non-homogeneous fluorescence of their principal surfaces under irradiation.

Application: to opthalmic lenses.

20 Claims, No Drawings

METHOD FOR DETERMINING THE SUITABILITY OF A TRANSPARENT MOULDED POLYMER ARTICLE FOR COLORING WITHOUT DEFECTS AND RESULTING ARTICLE

This application is a continuation of PCT Application No. PCT/FR00/00842 filed 5 Apr. 2000, which claims priority to French Application No. 99/04268 filed 6 Apr. 1999.

The present invention concerns in general terms a method for determining a priori if a colourless transparent moulded article, made of a polymer, such as an ophthalmic lens, is suitable to be coloured without coloration defects.

At present, ophthalmic lenses made from polymer material (organic glass) are commercially available in two forms, in the form of colourless ophthalmic lenses (clear organic glass lenses) and in the form of ophthalmic lenses coloured to varying shades (coloured organic glass lenses).

The colouring of ophthalmic lenses is generally performed by immersing the colourless clear glass lens in an aqueous colouring bath, containing a dispersion of pigments, maintained at a temperature of the order of 90° C.

Following this treatment, some ophthalmic lenses, although perfectly usable in their uncoloured state, may show defects in coloration, mainly variations in coloration which appear in the form of ferns, circles or loops, which make the commercial use of the coloured lens impossible. These defective coloured ophthalmic lenses cannot be recovered and must be discarded.

Such coloration defects are particularly found in ophthalmic lenses obtained from polymerizable compositions which have a significant shrinkage during polymerisation in the mould, generally equal to or greater than 7%, preferably equal to or greater than 10%, such as for example the lenses obtained by polymerisation of a polymerizable liquid composition comprising a diethylene glycol diallyl carbonate monomer (CR39®).

These coloration defects also more specifically concern ophthalmic lenses with positive strength.

The U.S. Pat. No. 4,303,701 discloses a method for marking plastic lenses by impregnation of a fluorescent material into the surface of the lens so that, when the lens is exposed to ultraviolet light, it becomes fluorescent, thus enabling the lens to be selectively identified. More exactly, the method disclosed in the U.S. Pat. No. 4,303,701 consists first of selecting, from lenses with two levels of quality, the lenses of higher quality and marking these selected lenses of higher quality by impregnation of a fluorescent material for subsequent identification. This method thus requires an initial step of sorting the lenses according to their quality, a step which is moreover not defined in the patent.

The patent EP-A-838850 discloses a method for revealing the surface defects of a substrate. The method consists of depositing a monomolecular layer of a fluorescent agent onto the surface of the substrate, then revealing the surface defects of the substrate by the luminous points resulting from light dispersion around the defects. This method is particularly suitable for determining defects on the surface of semiconductor substrates.

It would thus be desirable to have a method for determining, from a set of transparent moulded articles of clear organic glass, in particular ophthalmic lenses, those which are suitable for colouring without defects. This would thus avoid a significant wastage level in colouring the transparent moulded articles from clear organic glass, since the transparent moulded articles from clear organic glass which had not been selected, in particular ophthalmic lenses, would be of sufficient quality to be used in their uncoloured state.

According to the invention, it has been found that it is possible to determine a priori, before any colouring treatment, from a set of transparent moulded articles of clear organic glass, if these articles may be coloured without the risk of the appearance of coloration defects such as ferns, by placing in contact at least one principal surface of the colourless article with a solution of a fluorescent material in conditions such that the fluorescent material penetrates under the principal surface of the article, and irradiating the impregnated article with radiation which activates the fluorescence of the fluorescent material. The irradiation of the impregnated article reveals the presence of any defects corresponding to those which would appear during a subsequent colouring treatment. It is thus possible, at this stage, to perform a selection between the articles suitable for coloration without defects and unsuitable articles. Thus only the articles selected as suitable are subjected to the colouring treatment, and unsuitable articles are used for applications not requiring colouring.

The object of the invention is thus a method for determining the a priori suitability of colourless transparent moulded polymer articles, from a set of such articles, to produce after colouring treatment coloured transparent moulded articles, without coloration defects, characterized in that it comprises:

a) placing in contact at least one principal surface of the colourless articles of the set with a solution of a fluorescent material for a sufficient time to allow penetration of the fluorescent material under the principal surface of the articles;

b) irradiation of the impregnated articles by means of radiation which activates the fluorescence of the fluorescent material; and c) selection of the articles in the set into two sub-sets of which the first is composed of those articles of the set which show a homogeneous fluorescence of their principal surfaces under irradiation and the second is composed of those articles of the set which show a non-homogeneous fluorescence of their principal surfaces under irradiation.

Once this selection has been made, the articles of the first sub-set which show homogeneous fluorescence under irradiation may be subjected to colouring treatment with a near-certainty that a coloured article without coloration defects will be obtained.

The invention also relates to a method for producing coloured ophthalmic lenses from polymer material, characterized in that it comprises:

a) obtaining a set of ophthalmic lenses made of colourless polymer material;

b) placing in contact at least one principal surface of the ophthalmic lenses with a solution of a fluorescent material for a sufficient time to allow penetration of the fluorescent material under the principal surface of the ophthalmic lenses;

c) irradiation of the ophthalmic lenses by means of radiation which activates the fluorescence of the fluorescent material;

d) selection of the ophthalmic lenses in the set into two sub-sets of which the first is composed of the ophthalmic lenses which show a homogeneous fluorescence of their principal surfaces under irradiation and the second is composed of the ophthalmic lenses which show a non-homogeneous fluorescence of their principal surfaces under irradiation; and e) subjecting the ophthalmic lenses of the first sub-set to a colouring treatment.

In a variant of the method, one may, after the selection of the articles, subject them to a treatment to remove their fluorescence. Such a treatment may consist of irradiation of the selected articles with an appropriate UV radiation, such as UV-C radiation, or a chemical treatment such as dipping the articles in a bath of an agent for deactivating the fluorescent material. The recommended treatment for removing the fluorescent property is the chemical treatment, since the UV-C radiation tends to leave a slight yellow colour in the treated article.

The invention further concerns a transparent moulded polymer article, for example an ophthalmic lens, containing under one of its principal surfaces a thin impregnated layer of a deactivated fluorescent material. The thickness of this layer depends on the depth of impregnation of the fluorescent material, in general 0.1 to 5 $\mu$m, preferably 0.5 to 1.5 $\mu$m.

The solution of fluorescent material of the method of the invention is preferably an aqueous solution and the concentration in fluorescent material is generally between a few parts per million and a few tenths of one percent, preferably between 10 and 100 ppm, and typically of the order of 20 ppm.

For the solution of fluorescent material of the method of the invention, any known fluorescent material may be impregnated in the article. These include derivatives of hydrazines and of aliphatic amines, and more particularly dansyl cadaverine or dansyl ethylene diamine.

The fluorescent material in general has an absorption wavelength of between 200 and 400 nm and an emission wavelength of between 400 and 700 nm. The absorption (excitation) wavelength of the fluorescent material is preferably less than 380 nm, more preferably less than 320 nm and even more preferably less than 300 nm and its emission wavelength between 450 nm and 700 nm.

A particularly recommended fluorescent material is 5-dimethylaminonaphthalene-1-[N-(5-aminopentyl)] sulphonamide with formula:

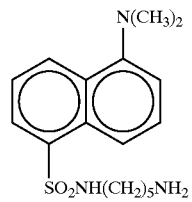

also named dansyl cadaverine.

The placing in contact of the uncoloured article with the solution of fluorescent material is preferably performed by immersing the article in the solution, but it is also possible to place only one principal surface of the article in contact with the solution, for example by depositing the solution by centrifugation.

In general, the solution of the fluorescent material, during the contact with the article, is at a temperature higher than the glass transition temperature of the polymer material of the article (for example, 83° C. for the material ORMA® of the ESSILOR Company) and is generally between 85° C. and 98° C., typically of the order of 95° C.

The length of the treatment of the article with the solution of fluorescent material must be sufficient for the fluorescent material to penetrate an adequate depth under the principal surface of the article, generally of the order of 0.1 to 5 $\mu$m and preferably from 0.5 to 1.5 $\mu$m. The length of treatment is generally of the order of 10 to 30 seconds, typically of the order of 20 seconds. Although longer treatment times may be used, it has been found that, beyond 2 minutes of treatment with the solution of fluorescent material, the effectiveness of any treatment for deactivation of the impregnated fluorescent material significantly decreases.

The step b) of irradiation of the articles impregnated with fluorescent material comprises the irradiation of the articles with any radiation which activates the fluorescence of the impregnated fluorescent material and preferably with a UV radiation whose wavelength corresponds to the absorption wavelengths of the impregnated fluorescent material. Thus an excitation UV radiation whose spectrum is centred around 350 nm is preferably used.

As stated above, the method of the invention preferably includes a step of deactivation of the fluorescent material impregnated into the selected articles.

This deactivation may be performed for example by irradiation of the article with UV-C radiation (wavelength ~250 nm) for about 20 seconds or by a chemical treatment such as immersion in a bath of a deactivation agent.

Suitable chemical deactivation agents include benzene alkyl sulfonate.

The chemical deactivation agent may be a carrier agent, in other words a transport activator. This case enables a greater diffusion of the fluorescent agent.

Without wishing to be limited by a particular mechanism, it is possible that part of the fluorescent agent is leached out (diffusion to the outside of the lens) while part penetrates into the interior.

When the material of the lens contains a UV absorber, the fluorescent agent is then inactivated by the UV absorber.

The chemical deactivation agents are generally used in solution form, in particular aqueous, at concentrations of 1 to 5% by weight.

The deactivation treatment is generally carried out with deactivation agent solutions at a temperature of 85 to 100° C., and with a duration of the order of 1 to 10 minutes depending on the deactivation agent and the solution temperature.

An example of such a bath is an aqueous solution 2% by weight in a benzene alkylsulfonate.

In this case of a 2% benzene alkylsulfonate bath, deactivation is achieved by dipping the article in the bath for 5 minutes at 95° C.

The colourless transparent polymer of the articles of the method of the invention may be any conventional colourless transparent polymer able to be impregnated by a fluorescent material.

These materials are preferably colourless transparent polymers with a significant shrinkage on moulding (polymerisation), generally 7% or more, and better 10% or more.

A preferred polymer is the material obtained by polymerisation of a polymerizable liquid composition, comprising a diethylene glycol diallyl carbonate monomer (CR39®), such as the ORMA® ophthalmic lenses of the ESSILOR Company.

The colourless transparent moulded polymer articles of the method of the invention are preferably articles with a positive optical strength, in particular ophthalmic lenses with a positive optical strength.

EXAMPLES

ORMA® ophthalmic lenses obtained by thermal polymerisation of diethylene glycol diallyl carbonate in an inorganic glass mould were tested by the method of the invention The detection test was performed as follows:

The lenses were immersed in an aqueous solution at 100° C. of 5-dimethylaminonaphthalene-1-[N-(5-aminopentyl)] sulphonamide (dansyl cadaverine) at a concentration of 20 ppm, for 2 minutes 30 seconds.

The lenses were removed from the solution, rinsed in cold water and dried with a soft cloth.

They were then illuminated with an ultraviolet lamp whose spectrum was centred around 350 nm.

The lenses were sorted according to whether or not they showed fluorescence heterogeneities.

Over 30 lenses of strength +6.00 dioptres, the test detected the presence of 21 defects of the whorl or circle type, and 9 lenses free from defects (showing homogeneous fluorescence).

After colouring, the 9 lenses were free from defects, and 19 lenses out of the 21 showed coloration defects.

The two other lenses which showed fluorescence defects (heterogeneities) did not show coloration defects.

The intensity of the fluorescence defect was in fact weak for these two lenses. The contrast of this defect after colouring was not detectable by the eye.

It would be possible to be less selective, for example by reducing the concentration of the fluorescent agent in the corresponding bath.

Over 30 lenses of strength +4.00 dioptres, the test detected the presence of 12 defects of the fern or circle type, and 18 lenses free from defects.

After colouring, the same proportions were observed.

Over 30 lenses of strength +2.00 dioptres, the test did not detect any whorl defects.

After colouring, there were no fern defects.

What is claimed is:

1. A method for determining suitability of transparent molded polymer articles to produce colored transparent molded articles comprising:
   a) obtaining a set of transparent molded polymer articles, each comprising at least a first principal surface;
   b) placing the first principal surface of each of the articles of the set in contact with a solution comprising a fluorescent material, for a sufficient time to allow penetration of the fluorescent material under the first principal surfaces of the articles;
   c) irradiating the articles to activate fluorescence of the fluorescent material; and
   d) selecting the articles in the set into a first subset composed of any articles that show a homogeneous fluorescence of the principal surface under irradiation and a second subset composed of any articles that show a non-homogeneous fluorescence of the principal surface under irradiation.

2. The method of claim 1, further comprising treating selected articles to deactivate fluorescence.

3. The method of claim 2, wherein treating consists of irradiating the selected articles with UV-C radiation.

4. The method of claim 2, wherein treating consists of dipping the selected articles in a bath of a chemical agent which deactivates fluorescence.

5. The method of claim 4, wherein the chemical deactivation agent is further defined as a benzene alkylsulfonate.

6. The method of claim 1, wherein the fluorescent material penetrates under the first principal surface of the articles to a depth of 0.1 to 5 $\mu$m.

7. The method of claim 6, wherein the fluorescent material penetrates under the first principal surface of the articles to a depth of 0.5 to 1.5 $\mu$m.

8. The method of claim 1, wherein irradiating comprises irradiation with UV radiation.

9. The method of claim 1, wherein the solution comprising fluorescent material is an aqueous solution at a concentration of 10 to 100 ppm.

10. The method of claim 9, wherein the solution comprising fluorescent material is an aqueous solution at a concentration of around 20 ppm.

11. The method of claim 1, wherein the solution comprising fluorescent material is at a temperature higher than the glass transition temperature of the polymer material of the articles.

12. The method of claim 11, wherein the temperature of the solution of the fluorescent material is from 85 to 98° C.

13. The method of claim 1, wherein the articles are further defined as comprised of a polymer material that has a polymerization shrinkage of at least 7%.

14. The method of claim 13, wherein the articles are further defined as comprised of a polymer material that has a polymerization shrinkage of at least 10%.

15. The method of claim 13, wherein the polymer material of the articles is obtained by polymerization of a polymerizable liquid composition comprising a diethylene glycol diallyl carbonate monomer.

16. The method of claim 1, wherein the molded articles are further defined as having a positive optical strength.

17. The method of claim 1, wherein the fluorescent material is selected from the derivatives of hydrazines and aliphatic amines.

18. The method of claim 1, wherein the molded articles are further defined as ophthalmic lenses.

19. A method for producing colored ophthalmic lenses from polymer material comprising:
   a) obtaining a set of ophthalmic lenses made of substantially colorless polymer material, each comprising at least a first principal surface;
   b) placing the first principal surface of each of the ophthalmic lenses of the set in contact with a solution comprising a fluorescent material, for a sufficient time to allow penetration of the fluorescent material under the first principal surfaces of the ophthalmic lenses;
   c) irradiating the ophthalmic lenses to activate fluorescence of the fluorescent material;
   d) selecting the ophthalmic lenses in the set into a first subset composed of any ophthalmic lenses that show a homogeneous fluorescence of the principal surface under irradiation and a second subset composed of any ophthalmic lenses that show a non-homogeneous fluorescence of the principal surface under irradiation; and
   e) subjecting the ophthalmic lenses of the first subset to a coloring treatment.

20. The method of claim 19, further comprising, after selecting the ophthalmic lenses and before the coloring treatment, treating selected articles to deactivate fluorescence.

* * * * *